United States Patent
Byrne et al.

(10) Patent No.: US 9,006,510 B2
(45) Date of Patent: Apr. 14, 2015

(54) GENETICALLY MODIFIED HEART VALVE XENOGRAFTS

(75) Inventors: Guerard W. Byrne, Rochester, MN (US); Christopher G. A. McGregor, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1329 days.

(21) Appl. No.: 12/306,186

(22) PCT Filed: Jun. 12, 2007

(86) PCT No.: PCT/US2007/071007
§ 371 (c)(1),
(2), (4) Date: Jul. 6, 2009

(87) PCT Pub. No.: WO2008/002767
PCT Pub. Date: Jan. 3, 2008

(65) Prior Publication Data
US 2009/0324674 A1 Dec. 31, 2009

Related U.S. Application Data

(60) Provisional application No. 60/817,830, filed on Jun. 29, 2006.

(51) Int. Cl.
| | | |
|---|---|---|
| G01N 33/00 | (2006.01) | |
| A01K 67/033 | (2006.01) | |
| C12N 9/10 | (2006.01) | |
| A61K 35/34 | (2006.01) | |
| A61K 35/12 | (2006.01) | |

(52) U.S. Cl.
CPC ......... *C12N 9/1051* (2013.01); *A01K 2217/075* (2013.01); *A01K 2227/101* (2013.01); *A61K 35/34* (2013.01); *A61K 2035/122* (2013.01)

(58) Field of Classification Search
USPC ....................................... 800/3, 15
See application file for complete search history.

(56) References Cited

U.S. PATENT DOCUMENTS

| | | |
|---|---|---|
| 4,106,129 A | 8/1978 | Carpentier et al. |
| 4,865,600 A | 9/1989 | Carpentier et al. |
| 5,633,076 A | 5/1997 | DeBoer et al. |
| 5,821,117 A | 10/1998 | Sandrin et al. |
| 6,210,957 B1 | 4/2001 | Carpentier et al. |
| 6,338,740 B1 | 1/2002 | Carpentier |
| 6,455,037 B1 | 9/2002 | Ioannou et al. |
| 6,547,827 B2 | 4/2003 | Carpentier et al. |
| 6,558,418 B2 | 5/2003 | Carpentier et al. |
| 6,561,970 B1 | 5/2003 | Carpentier et al. |
| 6,849,448 B1 | 2/2005 | D'Apice et al. |
| 6,878,168 B2 | 4/2005 | Carpentier et al. |
| 7,037,333 B2 | 5/2006 | Myers et al. |
| 2004/0171155 A1 | 9/2004 | d'Apice et al. |
| 2009/0324674 A1 | 12/2009 | Burne et al. |

FOREIGN PATENT DOCUMENTS

| | | |
|---|---|---|
| WO | WO 94/21799 | 9/1994 |
| WO | WO 2005/094587 | 10/2005 |

OTHER PUBLICATIONS

Gould and Auchincloss. Immunology Today 20(2):77-82, 1999; see p. 77, col. 2, 1st full par, lines 1-28.*
Azimzadeh et al. Hematology and Cell Therapy 38(4):331-343, 1997; see p. 1, par 2, lines 1-2 of the online printout of this article.*
Genbank Accession No. NW_928396, dated Sep. 30, 2005, 3 pages.
Genbank Accession No. XM_605800, dated Sep. 30, 2005, 3 pages.
Genbank Accession No. NM_177511, dated Jun. 3, 2007, 3 pages.
Genbank Accession No. J04989, dated Apr. 27, 1991, 3 pages.
"Edwards Launches New Mitral Magna Hear Valve in Europe," 2005, Edwards Lifesciences Corporation, News Release.
Arat et al., "In vitro Development of Bovine Nuclear Transer Embryos from Transgenic Clonal Lines of Adult and Fetal Fibroblast Cells of the Same Genotype," *Biol. Reprod.*, 2002, 66(6):1768-1774.
Arat et al., "Production of transgenic bovine embryos by transer of transfected granulosa cells into enucleated oocytes," Mol. Reprod. Dev., 2001, 60:20-26.
Cooper, "Clinical xenotransplantation—how close are we?" *The Lancet*, 2003, 362(9383):557-559.
Geisel et al., "In vivo Activity of Released cell Wall Lipids of Mycobacterium Bovis Bacillus Calmette-Guerin is Due Principally to Trehalose Mycolates," *J. Immunol.*, 2005, 174(8):5007-5015.
McKenzie et al., "Strategies to Overcome the Anti-Galα(1-3)Gal Reaction in Xenotransplantation," *Transplantation Proceedings*, 1996, 28(2):537.
Phelps et al., "Production of α1,3-Galactosyltransferase-Deficient Pigs," *Science*, 2003, 299(5605):411-414.
Rhoades et al., "Cell wall lipids from *Mycobacterium bovis* BCG are inflammatory when inoculated within a gel mixtures: Characterization of a new model of the granulomatous response to mycobacterial components," *Tuberculosis*, 2005, 85(3):159-176.
Sendai et al., "α1,3-Galactosyltransferase-Gene Knockout in Cattle using a Single Targeting Vector with loxP Sequences and Cre-Expressing Adenovirus," *Transplantation*, 2006, 81(5):760-766.
Sendai et al., "Heterozygous disruption of the α1,3-galactosyltransferase gene in cattle," *Transplantation*, 2003, 76(6):900-902
Shah et al., "Active site studies of bovine alpha1-3galactosyltransferase and its secondary structure prediction," *Biochem. Biophys. Acta.*, 2000, 1480:222-234.
Tearle et al., "The α-1,3-galactosyltransferase knockout mouse. Implications for xenotransplantation," *Transplantation*, 1996, 61(1):13-19.
Vanhove et al., "Intracellular expression in pig cells of anti-α1,3galactosyltransferase single-chain fv antibodies reduces galα1,3gal expression and inhibits cytotoxicity mediated by anti-gal xenoantibodies," *Transplantation*, 1998, 66(11):1477-1485.
WIPO Authorized Officer Kee Yeun Kim, International Search Report/Written Opinion, PCT/US2007/071007 mailed Nov. 7, 2007, 15 pages.

(Continued)

Primary Examiner — Marcia S Noble
(74) *Attorney, Agent, or Firm* — Fish & Richardson P.C.

(57) ABSTRACT

A method for producing a heart valve xenograft from bovine tissue expressing reduced or undetectable levels of I1-3 galactosyl transferase are provided.

2 Claims, No Drawings

(56) References Cited

OTHER PUBLICATIONS

WIPO Authorized Officer Ellen Moyse, International Preliminiary Report on Patentability, PCT/US2007/071007 mailed Jan. 15, 2009, 9 pages.

Adams et al., "Human membrane cofactor protein (MCP, CD 46) protects transgenic pig hearts from hyperacute rejection in primates," *Xenotransplantation*, 8(1):36-40, Feb. 2001.

Bartek et al., "Frame-mounted tissue heart vales: technique of construction," *Thorax*, 29:51-55, 1974.

Bovin et al., "Repertoire of human natural anti-glycan immunoglobulins. Do we have auto-antibodies?" *Biochim Biophys Acta.*, 1820(9):1373-1382, Epub Feb. 21, 2012.

Bracy et al., "Inhibition of xenoreactive natural antibody production by retroviral gene therapy," *Science.*, 281: 1845-1847, Sep. 18, 1998.

Byrne et al., "Identification of new carbohydrate and membrane protein antigens in cardiac xenotransplantation," *Transplantation*, 91(3):287-292, Feb. 15, 2011.

Byrne et al., "Protection of xenogeneic cardiac endothelium from human complement by expression of CD59 or DAF in transgenic mice," *Transplantation*, 60(10):1149-1156, Nov. 27, 1995.

Byrne et al., "Proteomic identification of non-Gal antibody targets after pig-to-primate cardiac xenotransplantation," *Xenotransplantation*, 15:268-276, Jul.-Aug. 2008.

Byrne et al., "Transgenic pigs expressing human CD59 and decay-accelerating factor produce an intrinsic barrier to complement-mediated damage " *Transplantation*, 63(1):149-155, Jan. 15, 1997.

Cesarman-Maus et al., "Autoantibodies against the fibrinolytic receptor, annexin 2, in antiphospholipid syndrome," *Blood*, 107(11):4375-4382, Jun. 1, 2006.

Cockerell et al., "Annexin A2: biology and relevance to the antiphospholipid syndrome," *Lupus*, 17(10):943-951, Oct. 17, 2008.

Cooper et al., "Alpha 1,3-galactosyltransferase gene-knockout pigs for xenotransplantation: where do we go from here?" *Transplantation*, 84(1):1-7, Jul. 15, 2007.

Cooper et al., "Oligosaccharides and disscordant xenotransplantation," *Immunol. Rev.*, 141:31-58, Oct. 1994.

Cozzi et al., "Characterization of pigs transgenic for human decay-accelerating factor," *Transplantation*, 64(10): 1383-1392, Nov. 27, 1997.

Davila et al., "T-cell responses during pig-to-primate xenotransplantation," *Xenotransplantation*, 13(1):31-40, Jan. 2006.

Diamond et al., "A human CD46 transgenic pig model system for the study of discordant xenotransplantation," *Transplantation*, 71(1):132-142, Jan. 15, 2001.

Diswall et al., "Structural characterization of alpha 1,3-galactosyltransferase knockout pig heart and kidney glycolipids and their reactivity with human and baboon antibodies," *Xenotransplantation*, 17(1):48-60, Jan.-Feb. 2010.

Diswall et al., "Studies on glycolipid antigens in small intestine and pancreas from alpha1,3-galactosyltransferase knockout miniature swine," *Transplantation*, 84(10):1348-1356, Nov. 27, 2007.

Esmon, "Structure and functions of the endothelial cell protein C receptor," *Crit Care Med.*, 32(5 Suppl):S298-S301, May 2004.

Fischer-Lougheed et al., "Gene therapy to inhibit xenoantibody production using lentiviral vectors in non-human primates," *Gene Ther.*, 14(1):49-57, Jan. 2007.

Harris et al., "Human and rodent decay-accelerating factors (CD55) are not species restricted in their complement-inhibiting activites," *Immunology*, 100(4):462-470, Aug. 2000.

Huflejt et al., "Anti-carbohydrate antibodies of normal sera: findings, surprises and challenges," *Mol Immunol.*, 46(15):3037-3049, Epub Jul. 15, 2009.

Johnson et al., "Cultivation and characterization of coronary microvascular endothelial cells: a novel porcine model using micropigs," *Microvasc Res.* 64(2):278-288, Sep. 2002.

Kagan et al., "Expression of complement regulatory factors using heterologous promoters in transgenic mice," *Transplant Proc.*, 26(3):1242, Jun. 1994.

Kamada et al., "Structural studies on a binding site for *Dolichos biflorus* agglutinin in the small intestine of the mouse," *J Biochem*, 109(1):178-183, Jan. 1991.

Kawakatsu et al., "Antithrombotic effect of an anti-glycoprotein IIB/IIIA antibody in primate lethal thrombosis," *Thromb Res.*, 70(3):245-254, May 1993.

Lerino et al., "Transfer of swine major histocompatibility complex class II genes into autologous bone marrow cells of baboons for the induction of tolerance across xenogeneic barriers," *Transplantation*, 67(8):1119-1128, Apr. 27, 1999.

Li et al., "The DXD motif is required for GM2 synthase activity but is not critical for nucleotide binding," *Glycobiology*, 11(3):217-229, Mar. 2001.

Liang et al., "Glycan arrays: biological and medical applications," *Curr Opin Chem Biol.*, 12(1):86-92, Epub Mar. 4, 2008.

Lila et al., "Gal knockout pig pericardium: new source of material for heart valve bioprostheses," *J Heart Lung Transplant.*, 29(5):538-543, Epub Dec. 29, 2009.

Liszewski et al., "Membrane cofactor protein (MCP or CD46): newest member of the regulators of complement activation gene cluster," *Annu Rev Immunol*, 9:431-455, 1991.

Malagolini et al., "Identification and characterization of the Sda beta 1,4,N-acetygalactosaminyltransferase from pig large intestine," *Glycoconj J.*, 11(2):89-95, Apr. 1994.

McGregor et al., "Cardiac xenotransplantation technology provides materials for improved bioprosthetic heart valves," *J Thorac Cardiovasc Surg.*, 141(1):269-275, Jan. 2011.

McGregor et al., "Human CD55 expression blocks hyperacute rejection and restricts complement activation in Gal knockout cardia xenografts," *Transplantation*, 93(7):686-692, Apr. 15, 2012.

Meri et al., "Human protectin (CD59), an 18,000-20,000 MW complement lysis restricting factor, inhibits C5b-8 catalysed insertion of C9 into lipid bilayers," *Immunology*, 71: 1-9, Sep. 1990.

Miyagawa et al., "Survey of glycoantigens in cells from $\alpha$1-3galactosyltransferase knockout pig using a lectin microarray," *Xenotransplantation*, 17(1):61-70, Jan.-Feb. 2010.

Mohiuddin et al., "B-cell depletion extends the survival of GTKO.hCD46Tg pig heart xenografts in baboons for up to 8 months," *Am J Transplant.*, 12(3):763-71. Epub Nov. 9, 2011.

Mohiuddin et al., "One-year heterotopic cardiac exnograft survival in a pig to baboon model," *Am J Transplant.*, 14(2):488-489, Epub Dec. 11, 2013.

Montiel et al., "Moloecular cloning, gene organization and expression of the human UDP-GalNAc:Neu5Aca2-3Ga1b-R b1,4-N-acetylgalactosaminyltransferase responsible for the biosynthesis of the blood group Sda/Cad antigen: evidence for an unusual extended cytoplasmic domain," *Biochem. J.*, 373:369-379, 2003.

Morelli and Thomson "Tolerogenic dendritic cells and the quest for transplant tolerance," *Nat Rev Immunol*, 7(8):610-621, Aug. 2007.

Morgan et al., "Homologous restriction" in complement lysis: roles of membrane complement regulators, *Xenotransplantation*, 12(4):258-265, Jul. 2005.

Nottle et al., "Production of homozygous alpha-1,3-galactosyltransferase knockout pigs by breeding and somatic cell nuclear transfer," *Xenotransplantation*, 14(4):339-344, Jul. 2007.

Paulson et al., "Sweet spots in functional glycomics," *Nat Chem Biol.*, 2(5):238-248, May 2006.

Piller et al., "Comparsion of the carbohydrate-binding specificities of seven N-acetyl-D-galactosamine-recognizing lectins," *Eur J Biochem.*, 191(2):461-466, Jul. 31, 1990.

Rescher and Gerke. "Annexins—unique membrane binding proteins with diverse function," *J Cell Sci.*, 117(Pt 13):2631-9, Jun. 1, 2004.

Reznicek et al., "A hemolytic reaction implication Sda antibody missed by immediate spin crossmatch," *Vox Sang*, 62(3):173-175, 1992.

Sharma et al., "Pig cells that lack the gene for alpha1-3 galactosyltransferase express low levels of the gal antigen," *Transplantation* 75(4):430-436, Feb. 27, 2003.

Simionescu, "Prevention of calcification in bioprosthetic heart valves: challenges and perspectives," *Expert Opin Biol Ther.*, 4(12):19671-1985, Dec. 2004.

Smith and Lowe, "Molecular cloning of a murine N-acetylgalactosamine transferase cDNA that determines expression

(56) References Cited

OTHER PUBLICATIONS of the T lymphocyte-specific CT oligosaccharide differentiation antigen," *J Biol Chem.*, 269(21):15162-15171, May 27, 1994.

Solanes et al., "Histological basis of the procine femoral artery for vascular research," *Anat Histol Embryol.*, 34(2):105-111, Apr. 2005.

Sonntag et al., "Tolerance to solid organ transplants through transfer of MHC class II genes," *J Clin Invest.*, 107(1):65-71, Jan. 2001.

Spitalnik et al., "The serology of Sda effects of tansfusion and pregnancy," *Vox Sang*, 42(6):308-312, 1982.

Tazelaar et al., "Comparsion of Ga1-and non-Ga1-mediated cardiac xenograft rejection," *Transplantation*, 91(9):968-975, May 15, 2011.

Tormey et al., "Red blood cell alloantibody frequency, specificity, and properties in a population of male military veterans," *Transfusion*, 48(10):2069-2076, Oct. 2008.

Van de Wouwer et al., "Thrombomodulin-protein C-EPCR system: integrated to regulate coagulation and inflammation," *Arterioscler Thromb Vasc Biol.*, 24(8):1374-1383, Epub Jun. 3, 2004.

van den Berg and Morgan, "Complement-inhibiting activites of human CD59 and analogues from rat, sheep, and pig are not homologously restricted," *J Immunol.*, 152(8):4095-4101, Apr. 15, 1994.

Ye et al., "The endothelial cell protein C receptor (EPCR) functions as a primary receptor for protein C activation on endothelial cells in artieries, veins, and capillaries," *Biochem Biophys Res Commun.*, 259(3):671-677, Jun. 16, 1999.

Yeh et al., "Investigation of potential carbohydrate antigen targets for human and baboon antibodies," *Xenotransplantation*, 17(3):197-206, May-Jun. 2010.

Zilla et al., "Prosthetic heart valves: Catering for the few," *Biomaterials*, 29(4):385-406. Epub Oct. 24, 2007.

International Preliminary Report on Patentability for Application No. PCT/US2011/031976, dated Nov. 6, 2012, 6 pages.

International Search Report and Written Opinion for Application No. PCT/US2011/031976, dated Jan. 2, 2012, 11 pages.

\* cited by examiner

GENETICALLY MODIFIED HEART VALVE XENOGRAFTS

CROSS-REFERENCE TO RELATED APPLICATIONS

This application is a National Stage application under 35 U.S.C. §371 and claims the benefit under 35 U.S.C. §119(a) of International Application No. PCT/US2007/071007, having an International Filing Date of Jun. 12, 2007, and entitled "Genetically Modified Heart Valve Xenografts," which claims the benefit of priority of U.S. Provisional Patent Application Ser. No. 60/817,830 having a filing date of Jun. 29, 2006 and entitled "Genetically Modified Heart Valve Xenografts," all of which are incorporated herein in their entirety.

BACKGROUND

1. Technical Field

This document relates to heart valve xenografts, and more particularly to heart valve xenografts from animals having a disruption in the endogenous α1-3 galactosyl transferase nucleic acid sequence.

2. Background Information

Prosthetic heart valves are used to replace damaged or diseased heart valves, including the aortic, mitral (bicuspid), tricuspid, and pulmonary heart valves. There are two basic types of prosthetic heart valves, mechanical and tissue valves. Mechanical heart valves use a pivoting mechanical closure to provide unidirectional blood flow. Mechanical valves do not wear out but they require life-long anticoagulation, with an increased incidence of thrombotic and hemorrhagic complications.

Tissue valves resemble native valves, and do not require life-long anticoagulation, but they wear out over time (in general after about 10 years). Much of the structure and many of the properties of original heart valves can be retained in transplants through use of heterograft (i.e., from the same species as the graft recipient) or xenograft (i.e., from a different species than the graft recipient) heart valve or heart tissue materials. Once implanted in an individual, a xenograft provokes hyperacute rejection (HAR), which occurs within minutes to hours of implantation. HAR can be overcome by a number of methodologies. If HAR is avoided, the organs can be rejected within a few days to weeks, even in the presence of a regimen of immunosuppressive agents that are effective at preventing allograft rejection. Xenografts can be chemically treated to reduce immunogenicity prior to implantation into a recipient or subjected to various physical treatments in preparation for implantation.

Heart valve xenografts typically are harvested from pig or cow heart tissues. Pig valves are often left intact and used as a direct replacement for the damaged valve of the recipient. Bovine heart valve xenografts are often made with bovine pericardium. Bovine heart valve xenografts are stronger than porcine xenografts but implant rejection is still a problem.

SUMMARY

The invention is based on the identification that bovine heart tissues and commercially available bovine heart valve xenografts express galactose α1,3 galactose β1,4N-acetylglucosamine trisaccharide (Gal α1-3Galβ1-4GlcNac; i.e., the α-gal antigen). Use of heart valve xenografts from transgenic cattle having reduced or no detectable α-gal antigen can reduce immunogenicity of the xenograft upon implantation and prolong durability of the xenograft.

One embodiment of the invention features a nucleic acid construct comprising a disrupted bovine α1-3 galactosyl transferase nucleic acid sequence, wherein the disruption is an alteration of the α1-3 galactosyl transferase nucleic acid sequence such that the disruption prevents expression of a functional α1-3 galactosyl transferase.

Another embodiment of the invention features a method of treating a patient having a defective heart valve. The method includes implanting into the patient a bovine heart valve xenograft; wherein cells of the xenograft contain a disruption of the endogenous α1-3 galactosyl transferase nucleic acid sequence. The heart valve xenograft can be a tricuspid valve, a mitral valve, an aortic valve, or a pulmonary valve or a portion of any of these. The heart valve xenograft can be made from bovine pericardial tissue.

In another embodiment, the invention features an article of manufacture that includes a bovine heart valve xenograft and a storage solution, wherein cells of the xenograft contain a disruption in the endogenous α1-3 galactosyl transferase nucleic acid sequence. The storage solution can be saline, a tissue preservative, or a cryoprotectant. The cryoprotectant can be dimethylsulfoxide, glycerol, albumin, monosaccharides, disaccharides, or serum.

The invention also features a method of preparing a xenograft heart valve for implantation into a human. The method includes providing a xenograft from a cow, wherein the xenograft includes a portion of a heart valve, wherein the cow's genome includes a disruption in the endogenous α1-3galactosyl transferase nucleic acid sequence, the disruption resulting in endothelial cells of the cow having reduced or no detectable expression of the α-gal antigen on their surface relative to cells of a control cow; and contacting the xenograft with a fixative. The fixative can be selected from the group consisting of gluteraldehyde, formaldehyde, adipic dialdehyde, an aliphatic diamine, an aromatic diamine, a carbodiimide, and a diisocyanate. Gluteraldehyde is a particularly useful fixative. The method further can include subjecting the xenograft to a freeze/thaw cycle. The method further can include contacting the xenograft with an agent selected from the group consisting of an anti-calcification agent, an anti-thrombotic agent, an antibiotic, and a growth factor. The method further can include sterilizing the xenograft.

In another embodiment, the invention features an article of manufacture that includes a heart valve xenograft from a cow, wherein the cow's genome includes a disruption in the endogenous α1-3 galactosyl transferase nucleic acid sequence, the disruption resulting in endothelial cells of the cow having reduced or no detectable expression of Gal α1-3Galβ1-4GlcNac on their surface relative to cells of a control cow. The xenograft can be attached to a stent.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This document provides methods and materials related to heart valve xenografts from transgenic cattle having a disruption in the endogenous α1-3 galactosyl transferase nucleic acid sequence. Provided herein are methods for making heart valve xenografts using tissue from transgenic cattle having a disrupted endogenous α1-3 galactosyl transferase nucleic acid sequence. Also provided are methods for treating a patient having a heart valve defect by implanting into the patient a bovine heart valve xenograft, wherein cells of the xenograft contain a disruption in the endogenous α1-3 galactosyl transferase nucleic acid sequence. Also provided are articles of manufacture, comprising a heart valve xenograft, wherein the cells of the xenograft contain a disruption in the endogenous α1-3 galactosyl transferase nucleic acid sequence.

Cattle Having Disruptions in the Endogenous α1-3 Galactosyl Transferase Nucleic Acid Sequence This document provides transgenic cattle whose genomes have a disruption in the endogenous α1-3 galactosyl transferase nucleic acid sequence. Such transgenic cattle can have reduced or no detectable α1-3 galactosyl transferase activity. Cells from such cattle can have reduced or no detectable expression of Gal α1-3Galβ1-4GlcNac (i.e., the α-gal antigen) on their surface relative to corresponding control, non-transgenic cattle. For example, cattle having a disruption in the endogenous α1-3 galactosyl transferase nucleic acid sequence can display at least 50 percent less α-gal antigen (e.g., less than 40 percent, less than 25 percent, less than 10 percent, or less than 3 percent expression) as compared to corresponding control, non-transgenic cattle.

The term "endogenous" as used herein in reference to a nucleic acid sequence, refers to any nucleic acid sequence that is naturally present in the genome of an organism. An endogenous nucleic acid sequence can comprise one or more gene sequences, intergenic sequences, portions of gene sequences or intergenic sequences, or combinations thereof. The term "endogenous α1-3 galactosyl transferase nucleic acid sequence" as used herein, refers to the entire α1-3 galactosyl transferase gene sequence, including introns, exons, and regulatory regions. An example of an endogenous bovine α1-3 galactosyl transferase gene sequence is available as Genbank sequence accession number NW_928396, from about nucleotide 23,572 to about nucleotide 99,939.

Any suitable method can be used to generate cattle whose genomes contain a disruption in the endogenous α1-3 galactosyl transferase nucleic acid sequence. For example, transgenic bovine cells can be used for nuclear transplantation. Transgenic cells can be produced by introducing a knock-out construct into wild-type bovine cells. As used herein, a "knock-out construct" refers to a nucleic acid construct that is designed to disrupt the endogenous bovine α1-3 galactosyl transferase nucleic acid sequence. A disruption can be anywhere in the endogenous bovine α1-3 galactosyl transferase nucleic acid sequence. Useful reference bovine sequences include those outlined in the NCBI GenBank sequence identification numbers XM_605800, NM_17751, J04989, and NW_928396. For example, a disruption can be within the sequence outlined in the NCBI GenBank identification number NW_928396. Examples of disruptions include, but are not limited to, deletions in the native gene sequence and insertions of heterologous nucleic acid sequences into the native gene sequence. Examples of insertions can include, but are not limited to, artificial splice acceptors coupled to stop codons or splice donors coupled to fusion partners such as GFP. A knock-out construct can contain sequences that are homologous to the α endogenous α1-3 galactosyl transferase nucleic acid sequence or to sequences that are adjacent to the endogenous α1-3 galactosyl transferase nucleic acid sequence. A knock-out construct can also contain a nucleic acid sequence encoding a selection marker (e.g., antibiotic resistance, a fluorescent reporter (e.g., GFP or YFP), or an enzyme (e.g., β-galactosidase)) operatively linked to a regulatory sequence (e.g., a promoter). A knock-out construct can include other nucleic acid sequences such as recombination sequences (e.g., loxP sequences, see Sendai, et al., *Transplantation*, (2006) 81 (5): 760-766), splice acceptor sequences, splice donor sequences, transcription start sequences, and transcription stop sequences. Disruptions in the endogenous α1-3 galactosyl transferase nucleic acid sequence can result in reduced expression of the gene or non-functional truncations or fusions of the encoded protein.

Transgenic cells having a disruption in the endogenous α1-3 galactosyl transferase nucleic acid sequence can be either adult or fetal cells and can be from primary or established cell lines. For example, transgenic fetal bovine fibroblasts can be fused with enucleated oocytes. Fused, activated oocytes can be cultured to the blastocyst stage, and implanted into a recipient. See, Arat, et al., *Biol. Reprod.*, (2002) 66 (6): 1768-1774, and DeBoer, et al., U.S. Pat. No. 5,633,076. Adult somatic cells of any cell type including, for example, granulosa cells and fibroblast cells, also can be used to produce transgenic cattle (Arat, et al., *Mol. Reprod. Dev.*, (2001) 60 (1): 20-26; and Arat, et al., (2002), supra, respectively.) Nuclei can be removed from genetically modified adult somatic cells, and transplanted into enucleated oocytes. After activation, the eggs can be cultured to the 2-8 cell stage, or to the blastocyst stage, and implanted into a suitable recipient (DeBoer, et al., supra). Transgenic cattle heterozygous for the disrupted α1-3 galactosyl transferase gene can be mated to produce homozygous transgenic cattle.

Transgenic cattle can be identified using suitable methods. For example, cells from animals obtained using nuclear transplantation can be assessed for endogenous α1-3 galactosyl transferase nucleic acid sequence disruption, α1-3 galactosyl transferase RNA expression, or α1-3 galactosyl transferase protein expression. For example, endogenous α1-3 galactosyl transferase nucleic acid sequence disruption can be identified using methods including southern blotting and PCR. α1-3 galactosyl transferase RNA expression can be determined using methods such as RT-PCR and fluorescent in situ hybridization. α1-3 galactosyl transferase protein expression can be determined using methods such as western blotting and immunohistochemistry. The methods for identifying transgenic cattle listed are intended to provide examples and are not in any way meant to limit the scope of the invention.

To determine if the α-gal antigen is present on the surface of cells from heterozygous or homozygous transgenic animals, tissue can be removed from the animal and then embedded using, for example, OCT (TISSUE-TEK, Sakura) embedding medium. Tissues can be sectioned, placed on glass slides, air-dried, and stored at −80° C. until use. The sectioned tissues can be stained for the α-gal antigen after fixing the sections in acetone, washing in water, blocking the slides, then incubating with the lectin, GSIB4. GSIB4 is commercially available (e.g., from Molecular Probes, Inc. (Eugene, Oreg.)). GSIB4 can be labeled. Suitable labels include, without limitation, radionuclides (e.g., $^{125}$I, $^{131}$I, $^{35}$S, $^{3}$H, $^{32}$P, $^{33}$P, or $^{14}$C), fluorescent moieties (e.g., fluorescein, PerCP, rhodamine, or phycoerythrin), luminescent moieties (e.g., QDot Nanoparticles from Quantum Dot Corporation, Palo Alto, Calif.), or enzymes (e.g., alkaline phosphatase or horseradish peroxidase). GSIB4 can be directly or indirectly labeled. Methods of indirect labeling can include, for example, conjugating the GSIB4 with biotin then contacting the GSIB4-biotin with avidin or streptavidin labeled with a molecule described above. Methods of detecting or quantifying a label depend on the nature of the label and are known in the art. Examples of detectors include, without limitation, x-ray film, radioactivity counters, scintillation counters, spectrophotometers, colorimeters, fluorometers, luminometers, and densitometers. Combinations of these approaches (including "multi-layer" assays) familiar to those in the art can be used to enhance the sensitivity of assays.

Obtaining Heart Valve Xenografts

As used herein, "heart valve xenograft" refers to a heart valve (e.g., aortic, tricuspid, bicuspid, or pulmonary) or a portion of a heart valve (e.g., a leaflet) comprising tissue from a species that is different from the graft recipient. A heart valve xenograft can comprise tissue from a transgenic cow having a disruption of the endogenous α1-3 galactosyl transferase nucleic acid sequence. Tissue for heart valve xenografts can be obtained by removing an intact heart from a transgenic cow and excising suitable heart tissues. Suitable heart tissues can include heart valves, portions of heart valves, and pericardial tissues. Tissues suitable for use in heart valve xenografts can also be non-heart tissues such as peritoneum.

Typically, bovine heart valve xenografts are fashioned from bovine pericardial tissue that is mounted on a flexible frame. There are many methods available for making a bovine heart valve xenograft. See, for example, the procedures discussed in U.S. Pat. Nos. 4,106,129, 4,865,600, 6,558,418, and 7,037,333. Bovine pericardium can be harvested using procedures known to the art.

It is particularly useful to collect the heart as soon as possible after slaughter of the animal. Typically, harvesting of the heart is performed in the cold (e.g., at about 5° C. to about 20° C.) and under strict sterile technique to minimize damage to the heart tissue. The heart can be placed in a suitable sterile isotonic or other tissue preserving solution.

In some embodiments, the xenograft can be supported using stents, rings or similar devices. For example, two or three leaflets can be sewn to a generally circular supporting silicone rubber or plastic frame or stent. The frame or stent can provide a stable support structure for the valve leaflets, and impart a degree of controlled flexibility to reduce stress on the leaflet tissue during valve closure. A biocompatible cloth covering can be provided on the frame or stent to provide sewing attachment points for the leaflet commissures and cusps. Similarly, a cloth covered suture ring also can be attached to the frame or stent to provide an attachment site for sewing the valve structure in position within the patient's heart during implantation.

The xenograft can be prepared for implantation in a human using known techniques. See, for example, U.S. Pat. Nos. 6,547,827, 6,210,957, 6,878,168, and 6,561,970. For example, the xenograft can be contacted with a fixative. Typically, this is performed to tan or crosslink the proteins within the extracellular components, to further diminish or reduce immunogenicity of the xenograft. Any fixative can be used for this treatment, and more than one fixing step can be performed or more than one fixative can be used. Suitable fixatives include, for example, gluteraldehyde, formaldehyde, adipic dialdehyde, an aliphatic diamine, an aromatic diamine, a carbodiimide, or a diisocyanate. Gluteraldehyde is particularly useful. For example, the xenograft can be contacted with a buffered solution containing from about 0.001 percent to about 5 percent (e.g., 0.1 percent to 5 percent) gluteraldehyde in buffer and having a pH of about 6 to 8 (e.g., about 7.4). Any suitable buffer can be used, including phosphate buffered saline or trihydroxymethylaminomethane, that can maintain control over the pH for the duration of the fixation. Typically, fixation can be performed from one to 14 days (e.g., one to five or three to five days).

Alternatively, the xenograft can be exposed to a fixative in a vapor form, including, but not limited to, a vaporized aldehyde fixative. For example, the xenograft can be exposed to a vaporized fixative, such as formaldehyde, having a concentration of about 0.001 percent to about 5.0 percent (e.g., about 0.01 percent to about 5.0 percent), and a pH of about 6 to 8 (e.g., about 7.4). Exposure to a vaporized fixative can result in less residual chemicals in the xenograft.

After fixation, the xenograft can be rinsed to remove residual chemicals and any unreacted aldehyde groups can be capped (e.g., by using 0.01-0.1 M glycine).

In some embodiments, the xenograft can be subjected to a freeze/thaw cycle to kill the xenograft's cells. The xenograft can be frozen using any known method. For example, the xenograft can be dipped into liquid nitrogen or frozen slowly by placing it in a freezer. The xenograft can be thawed by immersion in an isotonic saline bath at room temperature (about 25° C.) for about 10 minutes.

The xenograft can be coated with anticalcification agents, antithrombotic coatings, antibiotics, growth factors, or other drugs that can enhance the incorporation of the xenograft into the recipient.

In some embodiments, the xenograft can be sterilized. For example, the xenograft can be sterilized using liquid systems (e.g., with gluteraldehyde and formaldehyde), ethylene oxide or propylene oxide, or radiation.

In addition, a xenograft of the invention can be treated with polyethylene glycol (PEG), or treated with limited digestion by proteolytic enzymes such as ficin or trypsin to increase tissue flexibility.

The xenograft may be stored frozen until required for use. To freeze a xenograft, the xenograft can be contacted with a solution containing a cryoprotectant (e.g., dimethylsulfoxide (DMSO), glycerol, albumin, mono- and disaccharides, and/or serum such as fetal calf serum). For example, the solution can contain 0 percent to about 25 percent DMSO, 0 percent to about 25 percent glycerol, or 0 percent to about 50 percent albumin.

The heart valve xenograft can be implanted into damaged human hearts by those of skill in the art using known surgical techniques, including, for example, open heart surgery, or minimally invasive techniques such as endoscopic surgery and transluminal implantation. Specific instruments for performing such surgical techniques are known to those of skill in the art.

Articles of Manufacture

Xenografts can be combined with packaging materials and sold as articles of manufacture. Components and methods for producing articles of manufactures are well known. The articles of manufacture may combine one or more components described herein. For example, the xenograft can be packaged with a storage solution such as buffered saline, a tissue preservative, or a cryoprotectant, in a sterile container. In some embodiments, the xenograft is attached to a stent. Instructions describing how the xenograft can be used to treat a patient also can be included.

The invention will be further described in the following examples, which do not limit the scope of the invention described in the claims.

EXAMPLES

Example 1

Producing Transgenic Cattle

Fetal bovine fibroblasts are transfected with a knock-out construct containing a neomycin resistance gene flanked 1) on the 5' end by a sequence homologous to the 5' end of exon 8 (starting at nucleotide 94,699 of NW_928396) of the bovine α1-3 galactosyl transferase gene; and 2) on the 3' end by a sequence homologous to the 3' end of exon 9 (ending at nucleotide 99,939 of NW_928396) of the α1-3 galactosyl transferase gene. The transfected cells are selected with a concentration of G418 that is effective for killing untransfected cells. The selected cells are then clonally expanded and assessed for α1-3 galactosyl transferase gene disruption by PCR. Individual cells from selected clonal cell lines are fused with enucleated bovine oocytes using standard methods. Activated oocytes are grown for 7 days in vitro and then transferred to estrous-induced female cows (Arat, et al., (2002) supra; DeBoer, et al., supra). Calves are delivered by Caesarean section within one week of the end of the pregnancy term. For production of homozygous α1-3 galactosyl transferase knockout cattle using Cre-loxP-based vectors, see Sendai, et al., *Transplantation,* (2006) 81 (5): 760-766.

Example 2

Detecting α-gal Antigen in Bovine Heart Tissue

The presence of the Gal antigen is assessed on heart valves from wild-type cattle (i.e., no disruption in the α1-3 galactosyl transferase gene) and in cattle with a disruption in the α1-3 galactosyl transferase gene. Heart tissues and/or heart valves are dissected from the heart. Small portions of each are placed in OCT (TISSUE-TEK, Sakura) embedding medium and frozen at −80° C. For all samples, 5 micron sections are cut from frozen OCT embedded tissue and stained using standard immunohistological methods. Expression of the α-gal antigen (galactose α1,3 galactose β1,4 N-acetylglucosamine trisaccharide) is detected by binding of a horse radish peroxidase conjugated GSIB4 lectin (GSIB4-HRP) and visualized using standard DAB staining. The specificity of lectin binding for the α-gal antigen is demonstrated by competitive inhibition using 10 mM α-gal trisaccharide sugar (GSIB4-HRP+10 mM α-Gal sugar) to block lectin binding.

Commercially available bioprosthetic bovine heart valves are sectioned and stained for the Gal antigen as described above.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for providing a patient with a xenograft, said method comprising implanting into the heart of said patient a fixed bovine heart valve xenograft, wherein cells of said xenograft, prior to being fixed, contain a homozygous disruption in the endogenous α1-3 galactosyl transferase nucleic acid sequence and do not express α1-3 galactosyl transferase.

2. The method of claim 1, wherein said heart valve xenograft comprises pericardial tissue mounted on a flexible frame.

* * * * *